United States Patent [19]

Igarashi

[11] Patent Number: 4,707,477
[45] Date of Patent: Nov. 17, 1987

[54] TREATING AND PREVENTING AGENT FOR ISCHEMIC CARDIAC DISEASE AND ARRHYTHMIA

[75] Inventor: Toshiji Igarashi, Toyosato, Japan

[73] Assignee: Eisai Co., Ltd., Tokyo, Japan

[21] Appl. No.: 881,868

[22] Filed: Jul. 3, 1986

[30] Foreign Application Priority Data

Jul. 16, 1985 [JP]  Japan ................................. 60-155096

[51] Int. Cl.$^4$ .............................................. A61K 31/55
[52] U.S. Cl. .................................... 514/218; 514/929
[58] Field of Search ................................. 514/218, 929

[56]  References Cited

U.S. PATENT DOCUMENTS

| 4,189,484 | 2/1980 | Mizogami et al. | 514/218 |
| 4,426,382 | 1/1984 | Sato et al. | 514/218 |
| 4,578,389 | 3/1986 | Schickaneder et al. | 514/218 |
| 4,588,725 | 5/1986 | Neumann | 514/218 |
| 4,607,034 | 8/1986 | Mizogami et al. | 514/218 |

FOREIGN PATENT DOCUMENTS

| 60081 | 9/1982 | European Pat. Off. | 514/218 |
| 57-116052 | 7/1982 | Japan | 514/218 |

*Primary Examiner*—Douglas W. Robinson
*Attorney, Agent, or Firm*—Flynn, Thiel, Boutell & Tanis

[57]  ABSTRACT

A quinazoline compound having the below shown formula or a pharmaceutically acceptable salt thereof is useful for treatment and prevention of ischemic cardiac disease or arrhythmia.

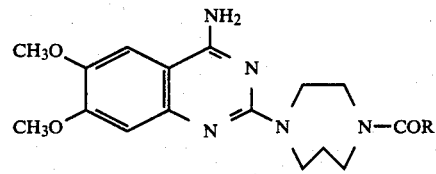

in which R is a lower alkyl, methoxy, a halogen, phenyl, a phenyl substituted with methanesulfonyl, furyl, styryl or a styryl substituted with a halogen, methoxy or methylenedioxy.

3 Claims, No Drawings

TREATING AND PREVENTING AGENT FOR ISCHEMIC CARDIAC DISEASE AND ARRHYTHMIA

The invention provides a method for treating and preventing ischemic cardiac disease or arrhythmia, which comprises administering to a patient suffering from the ischemic cardiac disease or arrhythmia or a human being a therapeutically effective amount of a quinazoline compound having the formula (I) or a pharmaceutically acceptable salt thereof.

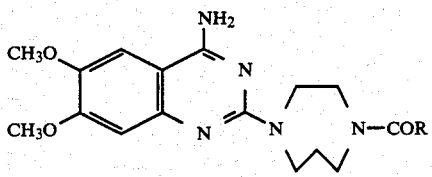

in which R is a lower alkyl, preferably having 1 to 6 carbon atoms; phenyl; phenyl substituted with methoxy, halogen or methanesulfonyl; furyl; styryl; or a styryl substituted with a halogen, methoxy or methylenedioxy.

The invention further provides use of a quinazoline compound as defined above or a pharmaceutically acceptable salt thereof for treatment and prevention of ischemic cardiac disease or arrhythmia. It also defines use of said quinazoline compound for preparation of a therapeutic and prophylactic agent against ischemic cardiac disease or arrhythmia.

It has been known that the quinazoline compound as used in the present invention is effective in treating and/or preventing various hypertensions including essential, renal or malignant hypertension (cf. Japanese patent publication No. 6156/1978, ibid. No. 7435/1978, and ibid. No. 7436/1978). It is believed that the above-mentioned effect of this compound is brought about by the α-receptor blocking function of the same.

We have studied pharmaceutical effects of the quinazoline compound (I), which is an effective hypotensive drug, other than the one as mentioned above and consequently found that it is unexpectedly effective in treating ischemic cardiac diseases, such as angina pectoris, or stenocardia, and myocardial infarction and various types of arrhythmia. The invention has been attained by this finding.

Accordingly it is an object of the present invention to provide a novel treating and/or preventive agent for ischemic cardiac diseases and arrhythmia.

The pharmaceutically acceptable salt as used in the present invention includes, for example, salts of inorganic acids, such as hydrochloride, hydrobromide, hydriodide and sulfate, and those of organic acids, such as maleate, fumarate, succinate, acetate, malonate, citrate and benzoate.

A typical example of the compound (I) of the present invention is the one wherein R in the formula (I) is a n-propyl group, i.e. 2-(N'-butyroylhomopiperazino)-4-amino-6,7-dimethoxyquinazoline[4-amino-2-(4-butyryl-hexahydro-1H-1,4-diazepin-1-yl)-6,7-dimethoxyquinazoline or hydrochloride of the same, which is generally called bunazosin hydrochloride, of the following structure:

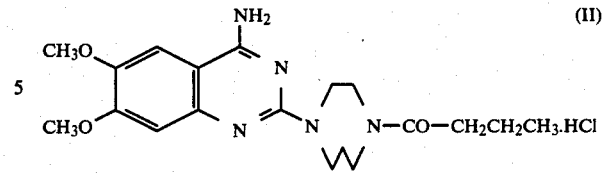

The compound (II) is present in the form of a white crystalline powder having no odor and a somewhat bitter taste. It is highly soluble in formic acid, not readily soluble in water and methanol, hardly soluble in absolute ethanol or n-butanol and almost insoluble in chloroform. Its melting point is approximately 273° C. (decomp.).

The compound of the present invention may be prepared by a process selected from among, for example, those described in Japanese patent publication No. 6156/1978, ibid. No. 7435/1978 and ibid No. 7436/1978, each as cited above.

For example, the process for the preparation of the same as described in Japanese patent publication No. 6156/1978 is as follows;

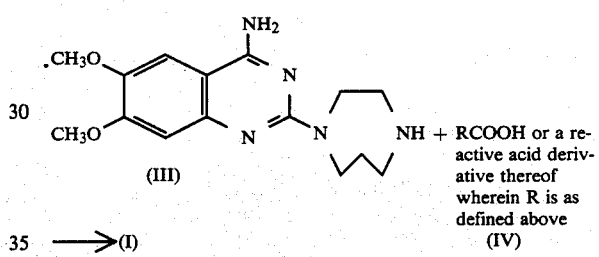

Namely, the compound (I) of the present invention may be obtained by reacting the compound (III) with a carboxylic acid or a reactive acid derivative thereof, such as an acid halide, an acid anhydride or an active ester, preferably in the presence of an acid acceptor such as triethylamine, an alkali hydrogencarbonate or pyridine in a conventional manner.

To further illustrate the effect of the compound of the invention, pharmacological experimental examples will be given below.

EXPERIMENTAL EXAMPLE 1

A dog was anesthetized with 50 mg/kg of sodium pentobarbital and a 2% CaCl₂ solution was intravenously injected into the femoral vein of the animal at a rate of 1.33 ml/min/10 kg. After 90 min, 0.1 mg, 0.2 mg and 0.3 mg of adrenaline were successively injected thereto intraveneously. As a result, ten animals among ten showed ventricular tachycardia or ventricular fibrillation.

Separately, the above procedure was repeated except that 0.5 mg/kg of bunazosin hydrochloride was intravenously injected 12 min before the intravenous injection of adrenaline. Consequently none among ten animals showed ventricular tachycardia nor ventricular fibrillation after intravenously injecting 0.1, 0.2 and 0.3 mg of adrenaline successively.

From a pathological viewpoint, the striated structure of a subject was damaged in the case where no bunazosin hydrochloride was previously administered. In contrast thereto, no change was observed in the case where bunazosin hydrochloride was previously administered.

EXPERIMENTAL EXAMPLE 2

A dog was anesthetized with 50 mg/kg of sodium pentobarbital and a 0.5% CaCl₂ solution was intravenously injected into the femoral vein of the animal at a rate of 1.33 ml/min/10 kg simultaneously with enemiasis of 25 g of sodium polystyrenesulfonate. After 30 min, 0.05 mg/kg of adrenaline was intravenously injected thereto. Creatinie phosphokinase (CPK) showed an increase of 82.0±20.1 thereby.

On the other hand, in the case where 0.5 mg/kg of bunazosin hydrochloride was previously administered, CPK determined 60 min after the injection of adrenaline was 85.1±15.6 showing no significant difference from the control.

The results of Experimental Examples 1 and 2 show an antiarrythmia effect (Example 1) and an antimyocardial infarction and antistenocardia effect (Example 2).

Results in a toxicity test as to the compound of the invention, bunazosin hydrochloride, are shown below in Table 1 in terms of acute toxicity, LD50, (mg/kg).

TABLE 1

| Animal | Sex | Oral | Intra-muscular | Intra-venous | Sub-cutaneous |
| --- | --- | --- | --- | --- | --- |
| ICR | ♂ | 1,201 | 660 | 57.0 | 730 |
| mouse | ♀ | 1,250 | 598 | 80.0 | 630 |
| Wistar | ♂ | 980 | 205 | 51.0~64.0 | 430 |
| rat | ♀ | 1,280 | 152 | 50.0 | 365 |

Table 1 suggests that the compound of the present invention is highly safe.

The compound of the present invention is available in treating and/or preventing ischemic cardiac diseases, such as myocardial infarction and angina pectoris as well as a variety of arrhythmia. As described above, the compound of the invention exhibits a very low toxicity and is highly safe. This can be administered to patients suffering from the above-mentioned diseases which require repeated administration for a prolonged period of time, which makes the present invention furthermore valuable.

In order to treat ischemic cardiac diseases and arrhythmia, the compound of the present invention may be orally or parenterally, e.g., intramuscularly, subcutaneously or intravenously administered. The dose of the same is not strictly limited but varies depending on the type and extent of the disease, age and body weight of the patient, concurrent treatment, if any, and the desired effect. It is generally administered in a dose of approximately 0.5 to 50 mg, preferably approximately 1 to 10 mg, still preferably approximately 1.5 to 6 mg to an adult a day.

The compound of the present invention may be formulated into various forms such as tablets, granules, capsules, injections and suppositories in a conventionally known manner in the art.

More precisely, a solid preparation such as tablets, coated tablets, granules, powders or capsules may be prepared by adding excipient(s) to the base optionally with other additives such as binder, disintegrating agent, lubricant, colorant and corrigent, if required, and formulating the obtained mixture into the desired form.

Examples of the excipient are lactose, corn starch, white sugar, glucose, sorbitol and crystalline cellulose. Examples of the binding agent are polyvinyl alcohol, polyvinyl ether, ethylcellulose, methylcellulose, gum arabic, tragacanth gum, gelatin, shellac, hydroxypropylcellulose, hydroxypropylstarch and polyvinylpyrrolidone. Examples of the disintegrating agent are starch, agar, powdery gelatin, crystalline cellulose, calcium carbonate, sodium hydrogencarbonate, calcium citrate, dextrin and pectin. Examples of the lubricant are magnesium stearate, talc, polyethylene glycol, silica and hardened vagetable oils. Examples of the colorant are those which are pharmaceutically acceptable. Examples of the corrigent are cacao powder, menthol, aromatic acids, peppermint oil, Borneo camphor and cinnamon powder. As a matter of course, the tablets or granules thus obtained may be further coated with, for example, sugar or gelatin, if desired.

An injection may be produced by adding various additives such as pH adjustor, buffer, stabilizer and preservative to the base and formulating the obtained mixture into an injection for subcutaneous intramuscular or intravenous administration in a conventional manner.

For a more complete understanding of the present invention, the following Preparation Examples each showing a pharmaceutical containing the compound of the present invention as an active ingredient will be given.

| Preparation Example 1: Capsule | |
| --- | --- |
| bunazosin hydrochloride | 70 g |
| mannitol | 300 g |
| corn starch | 450 g |
| lactose | 200 g |
| calcium stearate | 10 g |
| hydroxypropylcellulose | 30 g |

The above ingredients were mixed together in a conventional manner. Thus capsules each weighing 100 mg were prepared.

| Preparation Example 2: Tablet | |
| --- | --- |
| bunazosin hydrochloride | 10 g |
| corn starch | 200 g |
| lactose | 300 g |
| calcium carboxymethylcellulose | 150 g |
| polyvinylpyrrolidone | 70 g |
| talc | 70 g |
| microcrystalline cellulose | 200 g |

The above ingredients were mixed together in a conventional manner and the obtained mixture was compression-molded to thereby give tablets each weighing 100 mg.

The following Synthesis Example will show a process for synthesizing the compound of the present invention.

Synthesis Example 1: 2-[N'-(2-furoyl)homopiperazino]-4-amino-6,7-dimethoxyquinazoline (a) Synthesis of 2-homopiperazino-4-amino-6,7-dimethoxyquinazoline 17 g of 2-chloro-4-amino-6,7-dimethoxyquinazoline and 18.2 g of N-formylhomopiperazine were added to 170 ml of butanol and the mixture was heated under reflux for three hours. After the completion of the reaction, it was cooled and the crystals thus precipitated were filtered, washed with a small amount of ethanol, and air-dried. Thus 25 g of crude crystals were obtained. To 13 g of these crystals, 80 ml of 9% hydrochloric acid was added and the mixture was heated under reflux for 60 min. After the completion of the reaction, it was allowed to cool and the crystals thus precipitated were filtered and recrystallized from a mixture of methanol and ethanol.

Yield: 10.7 g (80.4%)
m.p.: 246–247° C.
Elemental analysis as $C_{15}H_{21}N_5O_2 \cdot 2HCl \cdot \frac{1}{2}H_2O$:

|  | C | H | N |
|---|---|---|---|
| calculated (%) | 46.74 | 6.29 | 18.17 |
| found (%) | 46.44 | 6.40 | 17.90 |

(b) Synthesis of 2-[N'-(2-furoyl)homopiperazino]-4-amino 6,7-dimethoxyquinazoline A solution of 3 g of 2-homopiperazino-4-amino6,7-dimethoxyquinazoline in 60 ml of acetone was added dropwise to another solution of 1.3 g of 2-furancarboxylic acid in 30 ml of acetone under stirring and ice-cooling. After the completion of the addition, the mixture was stirred for one hour to thereby complete the reaction. Then the crystals thus precipitated were filtered and recrystallized from a mixture of methanol and ethanol.

Yield: 3.1 g (70.4%).
m.p.: 278–280° C.
Elemental analysis as $C_{20}H_{23}N_5O_4 \cdot HCl$:

|  | C | H | N |
|---|---|---|---|
| calculated (%) | 55.36 | 5.59 | 16.15 |
| found (%) | 55.30 | 5.45 | 16.18 |

Table 2 shows compounds obtained by similar methods are the one described in the present Synthesis Example.

TABLE 2

| Syn. Ex. | R—CO— | Molecular formula m.p. (°C.) | Calculated / Found C | H | N |
|---|---|---|---|---|---|
| 2 | $CH_3CO-$ | $C_{17}H_{23}N_5O_3 \cdot HCl \cdot H_2O$ / 235~240 | 51.05 / 51.16 | 6.57 / 6.34 | 17.52 / 17.8 |
| 3 | $(CH_3)_2CHCO-$ | $C_{19}H_{27}N_5O_3 \cdot HCl \cdot \frac{1}{2}H_2O$ / 240~250 | 54.46 / 54.20 | 6.99 / 6.97 | 16.71 / 17.18 |
| 4 | $CH_3CH_2CH_2CO-$ | $C_{19}H_{27}N_5O_3 \cdot HCl$ / 280~282 | 55.66 / 55.40 | 6.90 / 6.89 | 17.09 / 16.79 |
| 5 | 2-Cl-C$_6$H$_4$-CO- | $C_{22}H_{24}ClN_5O_3 \cdot HCl \cdot H_2O$ / 235~240 | 53.22 / 53.18 | 5.49 / 5.79 | 14.11 / 13.61 |
| 6 | 2-OCH$_3$-C$_6$H$_4$-CO- | $C_{23}H_{27}N_5O_4 \cdot HCl$ / 225~235 | 58.27 / 57.78 | 5.97 / 6.09 | 14.78 / 14.32 |
| 7 | 4-CH$_3$SO$_2$-C$_6$H$_4$-CO- | $C_{23}H_{27}N_5O_5S \cdot HCl$ / 270~272 | 52.91 / 52.98 | 5.42 / 5.44 | 13.42 / 13.45 |
| 8 | 2,3-(OCH$_3$)$_2$-C$_6$H$_3$-CO- | $C_{24}H_{29}N_5O_5 \cdot HCl \cdot \frac{1}{2}H_2O$ / 220~225 | 56.18 / 56.06 | 6.10 / 6.29 | 13.65 / 13.46 |
| 9 | C$_6$H$_5$-CH=CH-CO- | $C_{24}H_{27}N_5O_3 \cdot HCl \cdot H_2O$ / 210~215 | 59.06 / 58.65 | 6.21 / 5.82 | 14.35 / 14.20 |
| 10 | 4-Cl-C$_6$H$_4$-CH=CH-CO- | $C_{24}H_{26}N_5O_3 \cdot HCl \cdot H_2O$ / 245~250 | 55.17 / 55.62 | 5.61 / 5.46 | 13.41 / 13.83 |

TABLE 2-continued

| Syn. Ex. | R—CO— | Molecular formula m.p. (°C.) | Elemental analysis (%) Calculated / Found | | |
|---|---|---|---|---|---|
| | | | C | H | N |
| 11 | CH₂—O—[benzene]—CH=CH—CO— (methylenedioxy) | $C_{25}H_{26}N_5O_5 \cdot HCl \cdot \frac{1}{2}H_2O$  235~240 | 57.51 / 57.80 | 5.42 / 5.62 | 13.42 / 13.52 |
| 12 | CH₃O, CH₃O, CH₃O trisubstituted —CH=CH—CO— | $C_{27}H_{31}N_5O_6 \cdot HCl \cdot \frac{1}{2}H_2O$  292~294 | 57.18 / 57.52 | 5.88 / 6.06 | 12.35 / 12.41 |

The embodiments of the invention in which an exclusive property or privilege is claimed are defined as follows:

1. A method for treating ischemic cardiac disease or arrhythmia, which comprises administering to a patient suffering from the ischemic cardiac disease or arrhythmia a therapeutically effective amount of a quinazoline compound having the formula

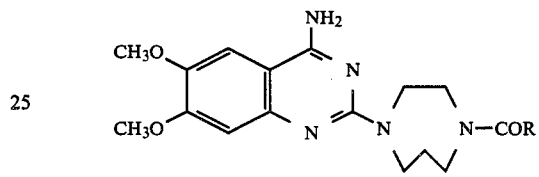

in which R is lower alkyl, phenyl, phenyl substituted with methoxy, halogen or methanesulfonyl, furyl, styryl or styryl substituted with halogen, methoxy or methylenedioxy, or a pharmaceutically acceptable salt thereof.

2. A method as claimed in claim 1, in which said compound is 2-(N'-butyroylhomopiperazino)-4-amino6,7-dimethoxyquinazoline.

3. A method as claimed in claim 1, in which said compound is 2-(N'-butyroylhomopiperazino)-4-amino6,7-dimethoxyquinazoline hydrochloride.

* * * * *